United States Patent [19] [11] 4,130,514
Enkoji et al. [45] Dec. 19, 1978

[54] SYNTHESIS OF PEPTIDES

[75] Inventors: Takashi Enkoji, Park Forest; Martin O. Skibbe, Kankakee, both of Ill.

[73] Assignee: Armour Pharmaceutical Company, Phoenix, Ariz.

[21] Appl. No.: 876,752

[22] Filed: Feb. 10, 1978

[51] Int. Cl.² .............. C08L 37/00; C07C 103/52; A61K 37/00
[52] U.S. Cl. .............. 260/8; 260/112.5 K; 424/177
[58] Field of Search .............. 260/8, 112.5 R; 424/177

[56] References Cited

U.S. PATENT DOCUMENTS 3,853,845 12/1974 Rousseau et al. .............. 260/112.5 R
3,915,949 10/1975 Colescott et al. .............. 260/112.5 R

FOREIGN PATENT DOCUMENTS 668250 2/1966 Belgium .............. 260/112.5 R
1220433 6/1973 Fed. Rep. of Germany .... 260/112.5 R
48-13117 4/1973 Japan .............. 260/112.5 R
484064 1/1970 Switzerland .............. 260/112.5 R

OTHER PUBLICATIONS

Blake et al., J. Med. Chem. 1974, 17, No. 2, pp. 233-235.

Primary Examiner—Delbert R. Phillips
Attorney, Agent, or Firm—Richard R. Mybeck; Carl C. Batz

[57] ABSTRACT

Peptides having adrenocorticotropic hormone activity and resin peptides useful in preparation of such peptides, particularly such peptides having asparagine at the carboxyl end thereof and more particularly such peptides having from 19 to 25 amino acids in their amino acid chains. The invention further involves new processes for the preparation of such peptides.

19 Claims, No Drawings

SYNTHESIS OF PEPTIDES

This invention relates to the synthesis of peptides, particularly peptides which are biologically active as adrenocorticotropic hormones, and to resin peptides useful in the preparation of such biologically active peptides. More specifically the invention relates to such biologically active peptides having shorter amino acid chain lengths than are found in natural peptides having adrenocorticotropic hormone activity.

BACKGROUND

It has long been known that certain biologically active substances can be obtained from the glands of animals and the substance so obtained utilized in the treatment of deficiencies of the human body. One such substance is the adrenocorticotropic hormone, commonly called ACTH, which for many years has been obtained from the pituitary glands of animals, particularly porcine and bovine pituitary glands.

For many years the art has eagerly awaited the discovery of more practical methods and compounds which enable the commercial synthesis of such peptides from other than natural sources. One such synthesis is set forth by Colescott, Kaiser, Bossinger and Cook in the U.S. Pat. No. 3,915,949 dated Oct. 28, 1975. Another is set forth in our co-pending application Ser. No. 672,459 filed Mar. 31, 1976.

Human adrenocorticotropic hormone (ACTH) is a polypeptide comprising 39 amino acids in a linear chain. The synthesis of peptides containing as many as 39 amino acids in its amino acid chain is a long and tedious synthesis providing many chances for error during the synthesis, and it would be a substantial advance in this art to provide a synthesis of such a peptide having a shorter amino acid chain length, especially if such desired peptide having a shorter amino acid chain length be found to have the same or greater biological activity than is contained in the natural hormone.

SUMMARY

We have discovered that by utilizing a benzhydrylamine resin and coupling aspartic acid to the resin at the carboxyl end of the peptide it is possible to produce new peptides having good adrenocorticotropic activity and containing asparagine at its carboxyl terminal position, and we have further found that it is possible to omit one or more intermediate amino acids heretofore thought to be necessary for peptides having adrenocorticotropic activity. Further, we find that, with asparagine at the carboxyl end of the peptide, activity may be enhanced by the selection of certain amino acids at the amino terminal of the peptide.

DETAILED DISCLOSURE

In general we use a solid phase synthesis utilizing a benzhydrylamine resin. This resin is prepared from resin beads obtained from the catalytic polymerization of styrene and divinylbenzene. These resin beads are subjected to a series of chemical reactions described by Pietta et al (P. G. Pietta, P. F. Cavallo, K. Takahashi and G. R. Marshall, J. Org. Chem. 39, 44 (1974)), and this results in a resin which contains benzhydrylamine groups, and which we call BHA resin. This resin may be represented by the structure:

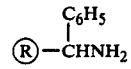

in which
Ⓡ is divinylbenzene crosslinked polystyrene, and $C_6H_5$ is a benzene ring.

This resin is now available from chemical supply houses.

Resin Peptide Synthesis

The amino acids are added one at a time to the insoluble BHA resin until the total desired peptide sequence has been built up on the resin. The α-amino groups of the amino acid derivatives are protected during addition to the resin by an acid labile protecting group which may be tertiarybutyloxycarbonyl (BOC), or amyloxycarbonyl (AMOC) or biphenyloxycarbonyl (BPOC). Some amino acids contain functional groups other than α-carboxyl and α-amino groups which may react with the amino acid derivatives being added causing the formation of undesirable by-products. These groups may be protected by blocking groups as follows:

The hydroxyl function of serine is protected by a benzyl or benzyl derivative group such as 4-methoxybenzyl, 4-methylbenzyl, 3,4-dimethylbenzyl, 4-nitrobenzyl, benzhydryl or an equivalent thereof. We use the term BZ to represent this benzyl or benzyl derivative group.

The hydroxyl function of tyrosine may be unprotected or may be protected by a BZ group as above described, or may be protected by a benzyloxycarbonyl or a benzyloxycarbonyl derivative such as 2-chlorobenzyloxycarbonyl or a 2-bromobenzyloxycarbonyl group or the equivalent thereof. We use the term Y to represent either no protective group (in which Y is H), a BZ group, a benzyloxycarbonyl group or a benzyloxycarbonyl derivative group.

The guanidino function of arginine may be protected by a nitro group, a tosyl group or an equivalent thereof. We use the character T to represent either a nitro group or a tosyl group or the equivalent thereof.

Where lysine is attached we prefer to use as the ε-amino protection agent, 2-chlorobenzyloxycarbonyl but may also use benzyloxycarbonyl (Z), 2-bromobenzyloxycarbonyl, or 2,4-dichlorobenzyloxycarbonyl. We use the symbol V to represent such a group.

The protective group preferred on the imidazole nitrogen of histidine is a benzyloxycarbonyl group but may be tosyl, dinitrophenyl, benzyl, benzyl derivative or no protective group. We use the symbol W to designate either no protective group or any of the named derivatives.

The α-carboxylic acid group of glutamic acid is protected by a BZ group.

Coupling agents (CA) such as dicyclohexylcarbodiimide (DCC) or other diimides may be used to assist the formation of peptide bonds. Alternatively, we may use the amino acid to be coupled in the form of its azide, anhydride or activated ester. The addition of each amino acid is followed by a deblocking or deprotection step in which an acid such as trifluoroacetic acid is used to remove the group protecting the α-amino group. The deprotected amino group, after neutralization and washing, is then ready for the addition of the next amino acid.

According to the accepted practice, the amino acid positions in peptides are numbered beginning with the position 1 at the amino terminus and ending with the carboxyl terminus.

In this invention the first coupling of an amino acid moiety is aspartic acid suitably in the form of its derivative which includes its protective group such as the BOC-L-aspartic acid α-benzyl ester. The last coupling of an amino acid moiety will be at position 1 and will be called Cycle 1.

For each coupling reaction we may use the selected amino acid with protective groups suitably in the form of a combined derivative. Such derivatives may be purchased or prepared by known procedures.

If we choose first to prepare a peptide having 25 amino acid residues, such peptide may be written as follows:

X—tyr—ser—met—glu—his—phe—arg—trp—gly—lys—pro—val—
1   2    3    4    5    6    7   8    9    10   11   12   13
gly—lys—lys—arg—arg—pro—val—lys—val—tyr—pro—asn
14  15  16  17  18  19  20  21  22  23  24  25 where X is D-ala or β-ala.

To prepare the 1–25 peptide, typical amino acid derivatives may be used as set forth in Table I.

TABLE I

| Cycle No. | Amino Acid Derivative |
|---|---|
| 25 | BOC-L-aspartic acid α-benzyl ester |
| 24 | BOC-L-proline |
| 23 | BOC-O-(2-bromobenzyloxycarbonyl)-L-tyrosine |
| 22 | BOC-L-valine |
| 21 | BOC-ε-(2-chlorobenzyloxycarbonyl)-L-lysine |
| 20 | BOC-L-valine |
| 19 | BOC-L-proline |
| 18 | BOC-$N^G$-tosyl-L-arginine |
| 17 | BOC-$N^G$-tosyl-L-arginine |
| 16 | BOC-ε-(2-chlorobenzyloxycarbonyl)-L-lysine |
| 15 | BOC-ε-(2-chlorobenzyloxycarbonyl)-L-lysine |
| 14 | BOC glycine |
| 13 | BOC-L-valine |
| 12 | BOC-L-proline |
| 11 | BOC-ε-(2-chlorobenzyloxycarbonyl)-L-lysine |
| 10 | BOC-glycine |
| 9 | BOC-L-tryptophan |
| 8 | BOC-$N^G$-tosyl-L-arginine |
| 7 | BOC-L-phenylalanine |
| 6 | BOC-N(im)-benzyloxycarbonyl)-L-histidine |
| 5 | BOC-L-glutamic acid γ-benzyl ester |
| 4 | BOC-L-methionine |
| 3 | BOC-O-benzyl-L-serine |
| 2 | BOC-O-(2-bromobenzyloxycarbonyl)-L-tyrosine |
| 1 | BOC-D-alanine or BOC-β-alanine |

If we choose to prepare a peptide having 24 amino acids we may omit the cycle 24; to prepare a peptide having 23 amino acids we may omit cycles 24 and 23; to prepare a peptide of 22 amino acids we may omit cycles 24, 23 and 22; to prepare a peptide of 21 amino acids we may omit cycles 24, 23, 22 and 21; to prepare a peptide of 20 amino acids we may omit cycles 24, 23, 22, 21 and 20; and to prepare a peptide of 19 amino acids we may omit cycles 24, 23, 22, 21, 20 and 19.

For any of these peptides having from 1–19 to 1–25 amino acids, the amino acid coupled at Cycle 1 may be D-ala or β-ala, and a formula describing all such chain lengths and amino acids may be written:

X-tyr-ser-met-glu-his-phe-arg-trp-gly-lys-pro-val-gly-lys-lys-arg-Q where
X is D-ala or β-ala, and
Q is asn, pro-asn, pro-val-asn, pro-val-lys-asn, pro-val-lys-val-asn, pro-val-lys-val-tyr-asn, or pro-val-lys-val-tyr-pro-asn.

In the following descriptive matter we give more explicit directions for preparing the peptides of the foregoing formulae starting with the 1-25 peptide and the reactants of Table I.

Preparation of a 25 Amino Acid Peptide

Cycle 25 - Coupling of BOC-L-aspartic acid α-benzyl ester.

The reaction vessel used in all steps of the resin peptide synthesis may be a glass vessel equipped with inlet ports at the top for addition of materials and a sintered glass disc at the bottom for removal of soluble excess reactants, by-products and solvents by filtration. The filtration can be performed either by vacuum or pressure. The contents of the vessel can be mixed by mechanical shaking of the entire vessel or by a mechanical stirrer.

In Cycle 25, the BHA resin is placed in the reaction vessel and washed with methanol and methylene chloride or any suitable organic solvent or any combination of these solvents. The washed BHA resin is resuspended in the solvent selected, and BOC-aspartic acid α-benzyl ester in an amount of 1 to 6 equivalents per equivalent of BHA resin is added. After mixing for 5 to 10 minutes, a coupling agent (CA) scuh as dicyclohexylcarbodiimide (DCC) may be added in the amount of 0.5 to 2.0 equivalents per equivalent of BOC-L-aspartic acid α-benzylester.

The BOC-L-aspartic acid α-benzyl ester may be coupled in the absence of a coupling agent if its activated ester, azide, or its symmetrical or mixed anhydride is used. The activated ester may be 2-nitrophenyl, 4-nitrophenyl, pentafluorophenyl, pentachlorophenyl, N-hydroxysuccinimido or any other such activated ester. These esters may be used in the amounts of 1 to 10 equivalents per equivalent of free amine of the BHA resin.

The reaction mixture consisting of BHA resin, solvent, BOC-L-aspartic acid α-benzyl ester and coupling agent or the reaction mixture of BHA resin, solvent and activated ester is mixed for a predetermined period of time and washed with a solvent such as methylene chloride, chloroform, methanol, dimethylformamide or acetic acid. The amount of wash solvents may be 2 to 20 ml for each gram of BHA resin used initially. The completeness of the reaction is determined by a ninhydrin test (E. Kaiser, et al, *Anal. Biochem.*, 34, 595 (1970)) on a test sample. If the test is positive, the coupling step is repeated.

The coupling reactions to produce BOC-L-aspartic acid α-benzyl ester resin may be illustrated by the following chemical equations:

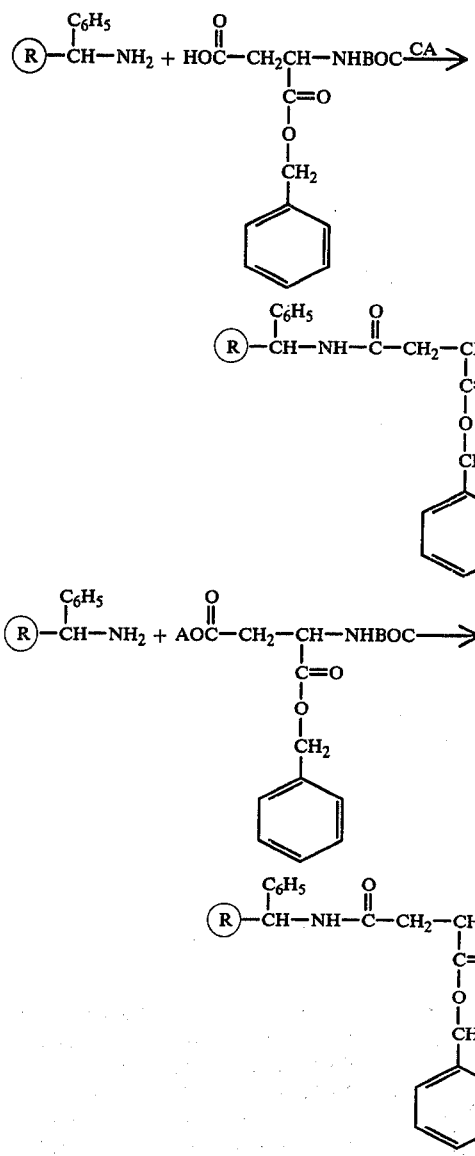

in which A represents 2-nitrophenyl, 4-nitrophenyl, pentafluorophenyl, pentachlorophenyl, succinimide or any such suitable activating group.

Deprotection of BOC-L-aspartic acid α-benzyl ester resin.

The BOC-L-aspartic acid α-benzyl ester resin from above may be deprotected by mixing with trifluoroacetic acid either alone or in combination with methylene chloride, chloroform, benzene, toluene or any other such solvent. The amount of TFA in the solvent can vary from 10 to 100% and the TFA-solvent mixture may vary from 2 to 20 ml per gram of BHA resin used initially. The reaction time may vary from 10 minutes to 4 hours, and the deprotection step is terminated by filtration to remove the TFA-solvent mixture. The residual TFA may be removed from the L-aspartic acid α-benzyl ester resin by washing with methylene chloride or chloroform, followed by methanol or ethanol and again with methylene chloride or chloroform. The washed resin, which is in the trifluoroacetate form, may be neutralized with a 5 to 30% solution of triethylamine in methylene chloride or chloroform. The amount of triethylamine solution may be 3 to 20 ml per gram of BHA resin used initially. Other amines of sufficient base strength may be substituted for triethylamine. The deprotection reaction may be illustrated by the following equation:

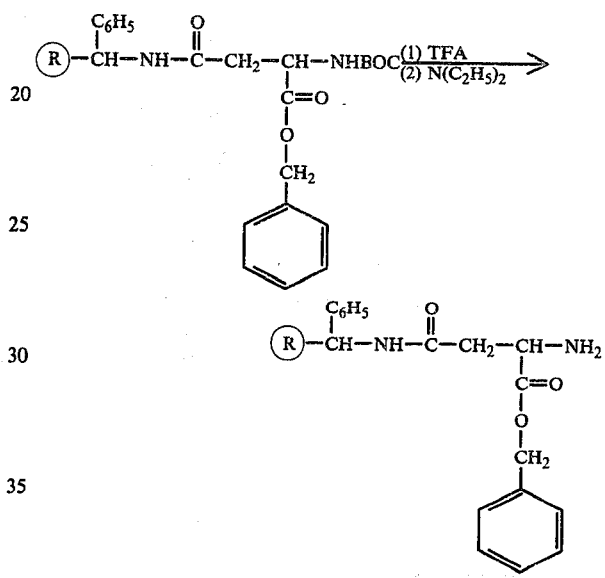

The product of the reaction according to the above formula may be represented in abbreviated form as follows:

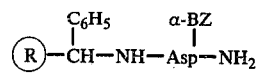

Cycle 24

The aspartyl BHA resin α-benzyl ester obtained from Cycle 25 may be resuspended in a solvent selected for the coupling reaction, and BOC-proline may be added. After mixing for 5 to 10 minutes, the coupling agent (CA) may be added. After mixing for the predetermined interval, the resin may be washed with methylene chloride, methanol, dimethylformamide or acetic acid. A sample may be tested by the ninhydrin test. If the test is positive, the coupling reaction is repeated. The amounts of reactants, solvents and reaction conditions may be essentially the same as those described for Cycle 25. The BOC group may be removed from the resin peptide by the deprotection method above described in connection with Cycle 25. The reactions of Cycle 24 may be illustrated by the following equations:

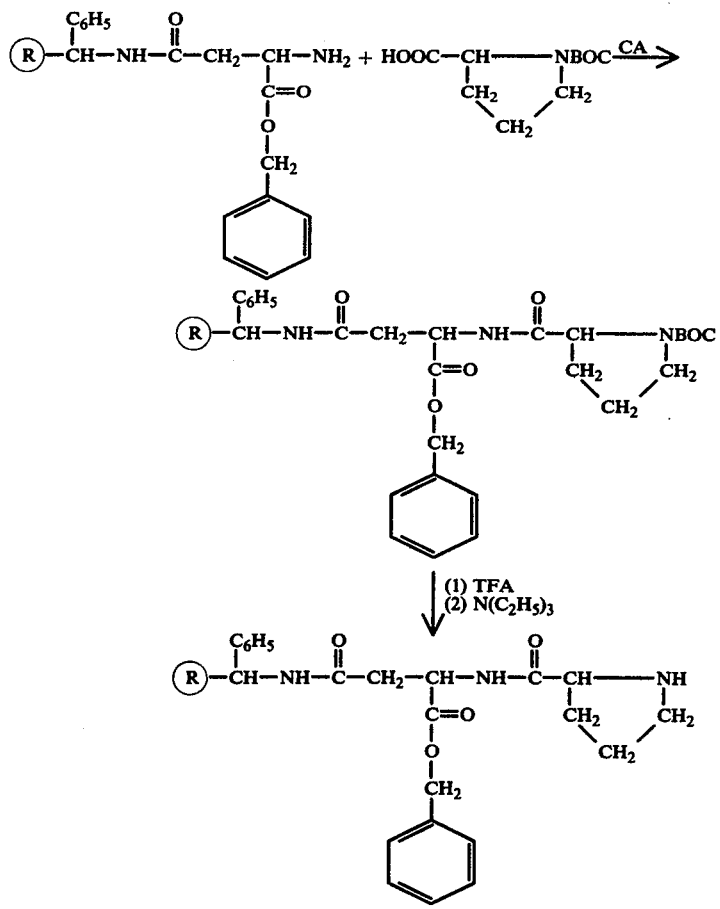

For convenience, we may represent this resulting resin peptide using abbreviated nomenclature as follows:

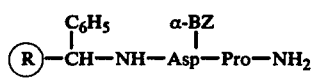

Cycle 23

In Cycle 23, the coupling and deprotection reactions may be performed in the same manner as in Cycle 24, except that BOC-O-(2-bromobenzyloxycarbonyl)-L-tyrosine is substituted for BOC-L-proline.

These reactions may be illustrated by the following equation:

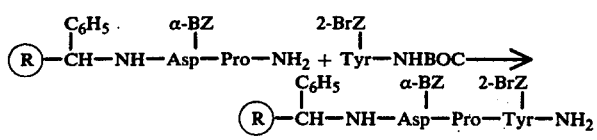

Cycles 22-1

In each of Cycles 22-1, the coupling and deprotection reactions may be conducted in the proper sequence using the methods described in Cycle 25 using BOC-L-valine in Cycle 22, BOC-ε-(2-chlorobenzyloxycarbonyl)-L-lysine in Cycle 21, BOC-L-valine in Cycle 20, BOC-L-proline in Cycle 19, BOC-N$^G$-tosyl-L-arginine in Cycles 18 and 17, BOC-ε-(2-chlorobenzyloxycarbonyl)-L-lysine in Cycles 16 and 15, BOC-glycine in Cycle 14, BOC-L-valine in Cycle 13, BOC-L-proline in Cycle 12, BOC-ε-(2-chlorobenzyloxycarbonyl)-L-lysine in Cycle 11, BOC-glycine in Cycle 10, BOC-L-tryptophan in Cycle 9, BOC-N$^G$-tosyl-L-arginine in Cycle 8, BOX-L-phenylalanine in Cycle 7, BOC-N(im)-benzyloxycarbonyl-L-histidine in Cycle 6, BOC-L-glutamic acid γ-benzyl ester in Cycle 5, BOC-L-methionine in Cycle 4, BOC-O-benzyl-L-serine in Cycle 3, BOC-O-(2-bromobenzyloxycarbonyl)-L-tyrosine in Cycle 2 and BOC-D-alanine in Cycle 1. After the coupling in Cycle 1, the deprotection may be performed as in Cycle 25, and the resin peptide resulting from Cycle 1 may be written:

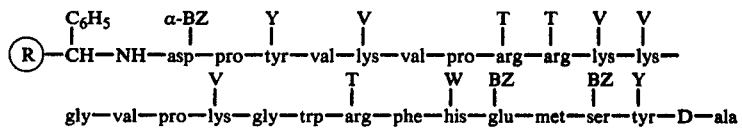

Resin Peptide Cleavage

The protection groups may be cleaved from the resin peptide resulting from Cycle 1 and the peptide itself may be cleaved from the resin by treatment with liquid hydrogen fluoride (HF). The HF cleavage reaction may be performed by treating a mixture of the resin peptide and anisole (0.5 to 5 ml for each gram of resin peptide) with liquid HF (2 to 20 ml for each gram of resin peptide) for 0.5 to 20 hours at −20 to +15° C.

After the reaction period, the excess HF may be removed by vacuum distillation, and the resulting mixture of peptide and resin beads may be washed with ethyl acetate or any other suitable solvent to remove residual anisole and HF. The peptide may be separated from the resin beads by extractive filtration with aqueous acetic acid. The extracts may be frozen and lyophilized to obtain the crude peptide.

The resulting compound after cleavage from the resin may be written:

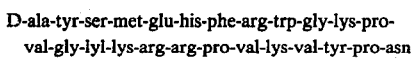

D-ala-tyr-ser-met-glu-his-phe-arg-trp-gly-lys-pro-val-gly-lyl-lys-arg-arg-pro-val-lys-val-tyr-pro-asn We call attention to the conversion of the protected aspartic acid residue to asparagine upon cleavage of the protecting group. To illustrate this more specifically, we may write the peptide containing the protected aspartic acid group as follows:

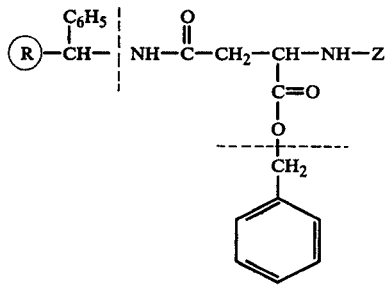

where Z is the remainder of the peptide chain and the dotted lines indicate where cleavage will occur.

The resulting peptide having asparagine at its carboxyl terminus can be written:

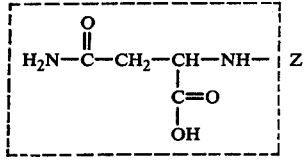

where the dotted line encloses the asparagine residue and Z is the remainder of the peptide chain.

Preparation of a 24 Amino Acid Peptide

To prepare the 24 amino acid peptide all of the 25 amino acid sequence may be repeated except that cycle 24 is omitted. The resulting peptide after HF cleavage may be written:

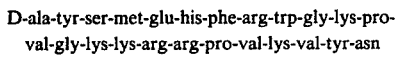

D-ala-tyr-ser-met-glu-his-phe-arg-trp-gly-lys-pro-val-gly-lys-lys-arg-arg-pro-val-lys-val-tyr-asn

Preparation of 1-23 to 1-19 Amino Acid Peptides

To prepare the 1-23 peptide all of the cycles in the 25 amino acid sequence may be repeated, except that cycles 24 and 23 are omitted. The resulting compound after HF cleavage may be written:

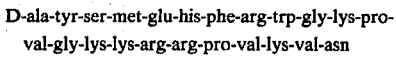

D-ala-tyr-ser-met-glu-his-phe-arg-trp-gly-lys-pro-val-gly-lys-lys-arg-arg-pro-val-lys-val-asn To prepare the 1-23, 1-22, 1-21, 1-20 and 1-19 peptides, the cycles in the 1-25 peptide synthesis above described may be repeated except that the cycles indicated below are omitted:

| Peptide Amino Acid Chain Length | Cycles Omitted |
|---|---|
| 23 | 24, 23 |
| 22 | 24, 23, 22 |
| 21 | 24, 23, 22, 21 |
| 20 | 24, 23, 22, 21, 20 |
| 19 | 24, 23, 22, 21, 20, 19 |

The formula for each of the above peptides are given as follows:

| Amino Acid Chain Length | Formula |
|---|---|
| 23 | D-ala-tyr-ser-met-glu-his-phe-arg-trp-gly-lys-pro-val-gly-lys-lys-arg-arg-pro-val-lys-val-asn |
| 22 | D-ala-tyr-ser-met-glu-his-phe-arg-trp-gly-lys-pro-val-gly-lys-lys-arg-arg-pro-val-lys-asn |
| 21 | D-ala-tyr-ser-met-glu-his-phe-arg-trp-gly-lys-pro-val-gly-lys-lys-arg-arg-pro-val-asn |
| 20 | D-ala-tyr-ser-met-glu-his-phe-arg-trp-gly-lys-pro-val-gly-lys-lys-arg-arg-pro-asn |
| 19 | D-ala-tyr-ser-met-glu-his-phe-arg-trp-gly-lys-pro-val-gly-lys-lys-arg-arg-asn |

In the formulae given above, D-ala is given as the amino acid at the amino terminal of the peptide. As above stated β-ala may also be used at the amino terminus.

Each of the above designated 1-19 to 1-25 peptides having asparagine at the carboxyl end and D-ala or β-ala at the amino end, when purified by ion-exchange chromatography on a carboxymethylcellulose column and gel filtration on a Sephadex column, exhibit adrenocorticotropic activity.

Concerning the preference as to amino acid chain lengths of the new peptides described herein, it is an advantage to prepare the peptides of shorter amino acid chain lengths certainly if the resulting peptides have a potency which is as great or greater than the peptides of longer amino acid chain lengths. From this standpoint we prefer to make and use the described peptides in the reverse order of their amino acid chain lengths. When amino acids are eliminated, the procedure for preparation of the peptide is simplified, the chances for side reactions and loss of yield are reduced, and the greater the number of amino acids that can be eliminated, the more practical the synthesis becomes.

To demonstrate in more detail the preparation of the new peptides of this invention we include the following specific examples:

EXAMPLE 1

Cycle 25

A 4.65 g. (0.002 mole) quantity of BHA resin was placed in a glass reaction vessel of a peptide synthesizer. A 40 ml. volume of methylene chloride was added, and after 10 minutes of mixing, 1.29 g. (0.004 mole) of BOC-aspartic acid α-benzyl ester was added. After 10 minutes of additional mixing, 1.8 ml. (0.004 mole) of 50% dicyclohexylcarbodiimide (DCC) was added. After 2 hours of mixing, the resin was filtered and washed twice with 25 ml. volumes of methylene chloride for 1 minute each. A ninhydrin test indicated that the coupling was complete.

To the washed and drained resin was added 30 ml. of 50% trifluoroacetic acid in methylene chloride (50% TFA), and after 30 minutes of mixing, the resin was washed twice for 1 minute each with 30 ml. volumes of methylene chloride, methanol and methylene chloride. Neutralization was accomplished with two 5 minute reactions with 30 ml. of 10% triethylamine in methylene chloride. The resin was washed twice with 30 ml. of methylene chloride for 1 minute each.

Cycle 24

The aspartic resin obtained from Cycle 25 was resuspended in 30 ml. of methylene chloride and 0.86 g. (0.004 mole) of BOC-L-proline was added. After mixing for 10 minutes, 1.8 ml. (0.004 mole) of 50% DCC in methylene chloride was added. After 2 hours of additional mixing, the resin was washed twice for 1 minute each with 25 ml. volumes of methylene chloride for 1 minute each. A ninhydrin test indicated that the coupling was complete. The resin was deprotected as in Cycle 25 to obtain a resin dipeptide.

Cycle 23

To the resin dipeptide obtained from Cycle 24 was coupled 1.98 g. (0.004 mole) of BOC-O-(2-bromobenzyloxycarbonyl)-L-tyrosine in the same manner described in Cycle 24. This protected resin tripeptide was deprotected with 30 ml. of 50% TFA as described in Cycle 25.

Cycles 22-2

The coupling procedures used in these cycles were the same as those described for Cycle 25 except for BOC-$N^G$-tosyl-L-arginine in Cycles 18, 17 and 8. This amino acid derivative was dissolved in 5 ml. of dimethylformamide and diluted to 30 ml. for the coupling reaction, and the mixing time after addition of 50% DCC was extended to 4 hours. The deprotection procedures for each step were identical to that described in Cycle 25. A 0.004 mole quantity of the following amino acid derivatives were used:

| Cycle No. | Wt., g. | Amino Acid Derivative |
|---|---|---|
| 22 | 0.87 | BOC-L-valine |
| 21 | 1.66 | BOC-ε-(2-chlorobenzyloxycarbonyl)-L-lysine |
| 20 | 0.87 | BOC-L-valine |
| 19 | 0.86 | BOC-L-proline |
| 18 | 1.70 | BOC-$N^G$-tosyl-L-arginine |
| 17 | 1.70 | BOC-$N^G$-tosyl-L-arginine |
| 16 | 1.66 | BOC-ε-(2-chlorobenzyloxycarbonyl)-L-lysine |
| 15 | 1.66 | BOC-ε-(2-chlorobenzyloxycarbonyl)-L-lysine |
| 14 | 0.70 | BOC-glycine |
| 13 | 0.87 | BOC-L-valine |
| 12 | 0.86 | BOC-L-proline |
| 11 | 1.66 | BOC-ε-(2-chlorobenzyloxycarbonyl)-L-lysine |
| 10 | 0.70 | BOC-glycine |
| 9 | 1.22 | BOC-L-tryptophan |
| 8 | 1.70 | BOC-$N^G$-tosyl-L-arginine |
| 7 | 1.06 | BOC-L-phenylalanine |
| 6 | 1.55 | BOC-N(im)-benzyloxycarbonyl-L-histidine |
| 5 | 1.35 | BOC-L-glutamic acid γ-benzyl ester |
| 4 | 1.00 | BOC-L-methionine |
| 3 | 1.18 | BOC-O-benzyl-L-serine |
| 2 | 1.98 | BOC-O-(2-bromobenzyloxycarbonyl)-L-tyrosine |

The resin peptide after Cycle 2 when deprotected, neutralized and dried, weighed 12.38 g.

Cycle 1

A 3.10 g. portion of this resin peptide was resuspended in 25 ml. of methylene chloride and 0.19 g. (0.001 mole) of BOC-D-alanine was added. After 10 minutes of mixing, 0.45 ml. (0.001 mole) of 50% DCC in methylene chloride was added. After mixing for 2 hours, the resin peptide was washed twice with 20 ml. of methylene chloride. The ninhydrin test indicated that the coupling was complete. The resin peptide was deprotected with 20 ml. of 50% TFA as described in Cycle 25. The product was dried in a vacuum oven at 40° C. to a constant weight to yield 3.10 g. of a resin peptide containing 25 amino acids.

EXAMPLE 2

Cycle 25

A 4.57 g. (0.002 mole) of BHA resin in the hydrochloride salt form was suspended in 50 ml. of a 50-50 mixture of methylene chloride and methanol in a glass reaction vessel of a peptide synthesizer. After mixing for 5 minutes, the solvent was removed by vacuum filtration through the sintered glass filter on one end of the reaction vessel. The resin was washed twice with 30 ml. volumes of methylene chloride for 1 minute each and neutralized by reacting twice with 30 ml. of 10% triethylamine in methylene chloride for 5 minutes each. The washing was repeated 3 times with 30 ml. of methylene chloride for 1 minute each. To the filtered resin was added 1.29 g. (0.004 mole) of α-t-BOC-aspartic acid α-benzyl ester. After 10 minutes of mixing, 1.80 ml. (0.004 mole) of 50% DCC in methylene chloride was added. After 2 hours of further mixing, the resin was filtered and washed for 5 minutes with 25 ml. of 10% triethylamine in methylene chloride followed by two washes of 1 minute each with 30 ml. volumes of methylene chloride. The ninhydrin test was negative indicating that the coupling was complete. To the washed and drained resin was added 30 ml. of 50% TFA, and after 1 minute of mixing, the resin was filtered and 30 ml. of the same reagent was added. Mixing was continued for 30 minutes and the resin was washed twice for 1 minute each with 30 ml. volumes of methylene chloride, methanol and methylene chloride. Neutralization was accomplished with two 5 minute reactions with 30 ml. of 10% triethylamine in methylene chloride. The resin was washed twice with 30 ml. of methylene chloride for 1 minute each.

Cycles 24 and 23

Both of these cycles were omitted.

Cycles 22-2

These cycles were performed in a consecutive manner using the coupling and deprotection procedures described in Cycle 25, Example 2. A 0.004 mole quantity of the same amino acid derivatives listed under Cycles 22-2 in Example 1 was used. The same procedure for dissolving and coupling BOC-$N^G$-tosyl-L-arginine were used. The resin peptide after Cycle 2 was not deprotected, and after thorough washing with methanol was dried to yield 11.60 g.

Cycle 1

A 3.80 g. quantity of dried resin peptide from Cycle 2 was deprotected in the same manner described for Cycle 25, Example 2 except that 20 ml. volumes of solvents and reagents were used throughout.

A 0.26 g. (0.0014 mole) quantity of BOC-D-alanine was added with 20 ml. of methylene chloride. After 10 minutes of mixing, 0.63 ml. (0.0014 mole) of 50% DCC in methylene chloride was added. After 2 hours of mixing, the resin peptide was reacted for 5 minutes with 20 ml. of 10% triethylamine in methylene chloride and washed twice for 1 minute each with 20 ml. of methylene chloride. A ninhydrin test indicated that the coupling was complete. The resin peptide was deprotected in the same manner described at the beginning of this Cycle 1 omitting the first wash with methanol and methylene chloride. Drying in a vacuum oven at 40° C to a constant weight yielded 3.84 g. of resin peptide containing 23 amino acids.

EXAMPLE 3

A 3.86 g. sample of the protected resin peptide from Cycle 2, Example 2 was deprotected in the same manner described in Cycle 1, Example 2. A 0.26 g. (0.0014 mole) quantity of BOC-$\beta$-alanine was coupled and deprotected in the same manner as in Cycle 1, Example 2. Drying in a vacuum oven at 40° C to a constant weight yielded 3.80 g of another resin peptide containing 23 amino acids.

EXAMPLE 4

Cycle 25

A 4.65 g. (0.002 mole) quantity of BHA resin was placed in a glass reaction vessel of a peptide synthesizer. A 1.29 g. (0.004 mole) quantity of BOC-aspartic acid $\alpha$-benzyl ester was coupled to the resin in the same manner described in Cycle 25, Example 1.

To the washed and drained resin was added 30 ml. of 100% TFA, and after 15 minutes of mixing, the resin was filtered and washed twice each for 1 minute with 30 ml. of methylene chloride, methanol and methylene chloride. Neutralization was accomplished with two 5 minute reactions with 30 ml. of 10% of triethylamine in methylene chloride. The resin was washed twice with 30 ml. of methylene chloride for 1 minute.

Cycles 24-19

These cycles were omitted.

Cycles 18-2

The coupling and deprotection procedures used in these cycles were the same as in Cycle 25, Example 4 using 0.004 mole of the following amino acid derivatives.

| Cycle No. | Wt., g. | Amino Acid Derivatives |
|---|---|---|
| 18 | 1.76 | AOC-$N^G$-tosyl-L-arginine* |
| 17 | 1.76 | AOC-$N^G$-tosyl-L-arginine |
| 16 | 1.66 | BOC-$\epsilon$-(2-chlorobenzyloxycarbonyl)-L-lysine |
| 15 | 1.66 | BOC-$\epsilon$-(2-chlorobenzyloxycarbonyl)-L-lysine |
| 14 | 0.70 | BOC-glycine |
| 13 | 0.87 | BOC-L-valine |
| 12 | 0.86 | BOC-L-proline |
| 11 | 1.66 | BOC-$\epsilon$-(2-chlorobenzyloxycarbonyl)-L-lysine |
| 10 | 0.70 | BOC-glycine |
| 9 | 1.22 | BOC-L-tryptophan |
| 8 | 1.76 | AOC-$N^G$-tosyl-L-arginine |
| 7 | 1.06 | BOC-L-phenylalanine |
| 6 | 1.55 | BOC-N(im)-benzyloxycarbonyl-L-histidine |
| 5 | 1.35 | BOC-L-glutamic acid $\gamma$-benzyl ester |
| 4 | 1.00 | BOC-L-methionine |
| 3 | 1.18 | BOC-O-benzyl-L-serine |
| 2 | 1.98 | BOC-O-(2-bromobenzyloxycarbonyl)-L-tryosine |

*AOC = t-amyloxycarbonyl

The resin peptide after Cycle 2 was dried in a vacuum oven at 40° C to a constant weight of 9.47 g.

Cycle 1

A 4.72 g. quantity of the deprotected resin peptide from Cycle 2 was resuspended in 25 ml. of methylene chloride and 0.38 g. (0.002 mole) of BOC-D-alanine was added. After 10 minutes of mixing, 0.9 ml. (0.002 mole) of 50% DCC in methylene chloride was added and after 30 minutes, the resin peptide was washed twice with 25 ml. of methylene chloride for 1 minute each. The ninhydrin test indicated that the coupling was complete, and the deprotection was performed with 25 ml. of 100% TFA as described in Cycle 25. The resin peptide, when dried to a constant weight in a vacuum oven, weighed 4.68 g. and contains 19 amino acids.

EXAMPLE 5

A 4.75 g. quantity of the resin peptide from Cycle 2, Example 4 was resuspended in 25 ml. of methylene chloride and to it was coupled 0.38 g. (0.002 mole) of BOC-$\beta$-alanine, and the resulting protected resin peptide was deprotected in the same manner described in Cycle 1, Example 4 to yield 4.70 g. of resin peptide containing 19 amino acids.

EXAMPLE 6

A 1.00 g. sample of dried resin peptide from Example 1 was placed in a Teflon Reaction vessel with 50 mg. each of L-tyrosine and L-tryptophan and 1 ml. of anisole. The vessel, equipped with a Teflon-coated magnetic stirring bar, was placed in a Dry Ice-acetone bath and 5 ml. of hydrogen fluoride gas was condensed into the vessel. The mixture was stirred at 0° C. for 45 minutes and the hydrogen fluoride was removed at reduced pressure at room temperature. The residue was triturated with 50 ml. of ethyl acetate and the solids were collected in a Buchner funnel. The washing was repeated three times in the funnel with 25 ml. volumes of ethyl acetate. The peptide was extracted by percolating 20 ml. of glacial acetic acid through the filter over a 10 minute period. The lumps were broken up with a glass stirring rod, and the extraction was repeated four times with 10 ml. volumes of glacial acetic acid. The combined acetic acid extracts were frozen and lyophilized to yield 0.309 g. of crude [D-ala$^1$, asn$^{25}$]-ACTH-(1-25).

EXAMPLE 7

A 2.00 g. sample of dried resin peptide from Example 2 was cleaved in the same manner as described in Example 6 using 50 mg. each of L-tyrosine and L-tryptophane, 2 ml. of anisole and 10 ml. of liquid hydrogen fluoride. After 45 minutes of stirring at 0° C, the hydrogen fluoride was removed by distillation at reduced pressure. The residue was triturated with 80 ml. of ethyl acetate and the solids were collected in a Buchner funnel. The solids were washed three times with 40 ml. volumes of ethyl acetate. The peptide was extracted by percolating four 25 ml. volumes of glacial acetic acid through the filter, breaking up the lumps with a glass rod. The acetic rod extracts were combined and lyophilized to yield 0.799 g. of crude [D-ala¹,asn²³]-ACTH-(1-23).

EXAMPLE 8

A 2.00 g. sample of dried resin peptide from Example 4 was cleaved with liquid hydroen fluoride in the same manner described in Example 7. The yield was 0.806 g. of crude [D-ala¹,asn¹⁹]-ACTH-(1-19).

EXAMPLE 9

A solution of 0.202 g. of crude peptide from Example 6 and 1.2 g. of urea in 20 ml. of pH 4.0 ammonium acetate buffer (conductivity 4.0 millimhos, 25° C) was filtered. The filtrate was placed on a CM52 carboxymethylcellulose chromatographic column (bed volume 3.5 ml.) prepared in the same buffer. The column was eluted with 125 ml. of pH 6.5 ammonium acetate buffer (conductivity 4.0 millimhos, 25° C), followed by 50 ml. of pH 6.9 ammonium acetate buffer (conductivity 16 millimhos, 25° C). The flow rate was approximately 1 ml. per minute and 10 ml. fractions were collected. The fractions comprising the major peak, determined by the optical density at a wavelength of 280 nanometers on an ultraviolet absorptiometer, were combined and lyophilized. The lyophilized material was dissolved in 5 ml. of 0.5 molar acetic acid and desalted by gel filtration through a fine mesh Sephadex G-25 column (bed volume 100 ml.) prepared with the same solvent. The column was eluted with 0.5 molar acetic acid at a flow rate of approximately 1 ml. per minute and 5 ml. fractions were collected. Again, the major peak fractions, determined by ultraviolet absorption at 280 nanometers, were combined and lyophilized to yield 0.190 g. of purified [D-ala¹,gln²⁵]-ACTH-(1-25). This peptide was found to have adrenocorticotropic activity.

EXAMPLE 10

A 0.201 g. sample of crude peptide from Example 7 was subjected to the same procedure described in Example 9. The yield was 0.105 g. of purified [D-ala¹,asn²³]-ACTH-(1-23). This peptide was found to have adrenocorticotropic activity.

EXAMPLE 11

A 0.207 g. sample of crude peptide from Example 8 was subjected to the same procedure described in Example 9. The yield was 0.073 g. of purified [D-ala¹,asn¹⁹]-ACTH-(1-19). This peptide was found to have adrenocorticotropic activity.

While we have described in detail only certain embodiments of our invention it will be apparent to those skilled in this art that many other embodiments may be utilized and many changes and variations may be made, it being understood that all such embodiments, changes and variations are within the spirit of the invention and within the scope of the appended claims.

What is claimed is:

1. A peptide having the structure

X—tyr—ser—met—glu—his—phe—arg—trp—gly—lys—
   1    2    3    4    5    6    7    8    9    10   11
              —pro—val—gly—lys—lys—arg—arg—Q
               12   13   14   15   16   17   18 in which

X is D-ala or β-ala, and

Q is asn, pro-asn, pro-val-asn, pro-val-lys-asn, pro-val-lys-val-asn, pro-val-lys-val-tyr-asn, or pro-val-lys-val-tyr-pro-asn.

2. A peptide as set forth in claim 1 in which Q is asn.
3. A peptide as set forth in claim 1 in which Q is pro-asn.
4. A peptide as set forth in claim 1 in which Q is pro-val-asn.
5. A peptide as set forth in claim 4 in which Q is pro-val-lys-asn.
6. A peptide as set forth in claim 1 in which Q is pro-val-lys-val-asn.
7. A peptide as set forth in claim 1 in which Q is pro-val-lys-val-tyr-asn.
8. A peptide as set forth in claim 1 in which Q is pro-val-lys-val-tyr-pro-asn.
9. A peptide as set forth in claim 1 in which X is D-ala.
10. A peptide as set forth in claim 1 in which X is β-ala.
11. A resin peptide having the structure

```
         C6H5    α-BZ    Y       V              T    T    V    V
          |       |      |       |              |    |    |    |
   (R)—CH—NH—asp—pro—tyr—val—lys—val—pro—arg—arg—lys—lys—
                25   24  23  22  21  20  19  18   17   16   15
                              V            T        W   BZ      Bz   Y
                              |            |        |    |       |   |
        gly—val—pro—lys—gly—trp—arg—phe—his—glu—met—ser—tyr—X
         14   13  12   11  10   9    8    7    6    5    4    3   2   1
``` where (R) is divinylbenzene crosslinked polystyrene, BZ is benzyl, p-methoxybenzyl, p-chlorobenzyl, p-nitrobenzyl or benzylhydryl, Y is H, benzyl, benzyloxycarbonyl, benzyloxycarbonyl, 2-chlorobenzyloxycarbonyl or 2-bromobenzyloxycarbonyl, V is 2-chlorocarboxybenzyloxy, benzyloxycarbonyl, 2-bromocarboxybenzyloxy or 2,4-dichlorocarbobenzyloxy, and X is D-ala or β-ala.

12. A peptide having the structure

D-ala-tyr-ser-met-glu-his-phe-arg-trp-gly-lys-pro-val-bly-lys-lys-arg-arg-asn.

13. A peptide having the structure

β-ala-tyr-ser-met-glu-his-phe-arg-trp-gly-lys-pro-val-gly-lys-arg-arg-asn.

14. A resin peptide having the structure

```
         C6H5    α-BZ    Y       V              T    T    V    V
          |       |      |       |              |    |    |    |
   (R)—CH—NH—asp—tyr—val—lys—val—pro—arg—arg—lys—lys—gly—
```

-continued

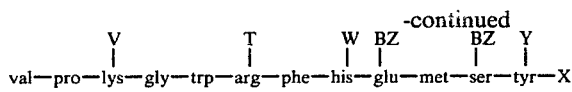

where
- Ⓡ is divinylbenzene crosslinked polystyrene, BZ is benzyl, p-methoxybenzyl, p-chlorobenzyl, p-nitrobenzyl or benzylhydryl,
- y is H, benzy, benzyloxycarbonyl, 2-chlorobenzyloxycarbonyl or 2-bromobenzyloxycarbonyl,
- v is 2-chlorocarboxybenzyloxy, benzyloxycarbonyl, 2-bromocarboxybenzyloxy or 2,4-dichlorocarbobenzyloxy, and
- X is D-ala or β-ala.

15. A resin peptide having the structure

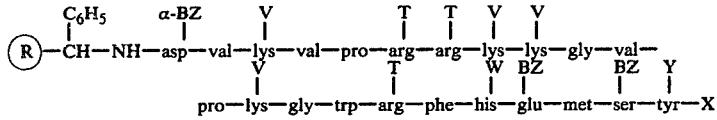

where
- Ⓡ is divinylbenzene crosslinked polystyrene,
- BZ is benzyl, p-methoxybenzyl, p-chlorobenzyl, p-nitrobenzyl or benzylhydryl,
- Y is H, benzyl, benzyloxycarbonyl, 2-chlorobenzyloxycarbonyl or 2-bromobenzyloxycarbonyl,
- V is 2-chlorocarboxybenzyloxy, benzyloxycarbonyl, 2-bromocarboxybenzyloxy or 2,4-dichlorocarbobenzyloxy, and
- X is D-ala or β-ala.

16. A resin peptide having the structure

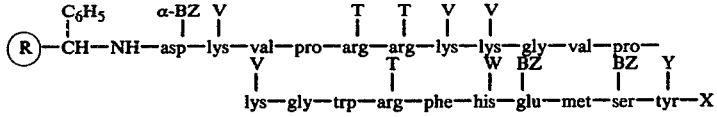

where
- Ⓡ is divinylbenzene crosslinked polystyrene,
- BZ is benzyl, p-methoxybenzyl, p-chlorobenzyl, p-nitrobenzyl or benzylhydryl,
- Y is H-benzyl, benzyloxycarbonyl, 2-chlorobenzyloxycarbonyl or 2-bromobenzyloxycarbonyl,
- V is 2-chlorocarboxybenzyloxy, benzyloxycarbonyl, 2-bromocarboxybenzyloxy or 2,4-dichlorocarbobenzyloxy, and
- X is D-ala or β-ala.

17. A resin peptide having the structure

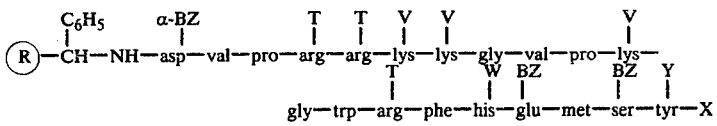

where
- Ⓡ is dinvylbenzene crosslinked polystyrene,
- BZ is benzyl, p-methoxybenzyl, p-chlorobenzyl, p-nitrobenzyl or benzylhydryl,
- Y is H, benzyl, benzyloxycarbonyl, 2-chlorobenzyloxycarbonyl or 2-bromobenzyloxycarbonyl,
- V is 2-chlorocarboxybenzyloxy, benzyloxycarbonyl, 2-bromocarboxybenzyloxy or 2,4-dichlorocarbobenzyloxy, and
- X is D-ala or β-ala.

18. A resin peptide having the structure

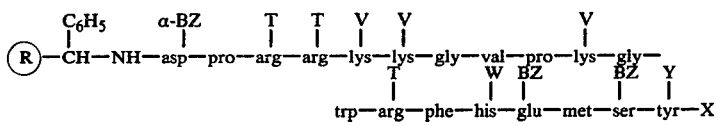

where
- Ⓡ is dinvylbenzene crosslinked polystyrene,
- BZ is benzyl, p-methoxybenzyl, p-chlorobenzyl, p-nitrobenzyl or benzylhydryl,
- Y is H,benzyl,benzyloxycarbonyl, 2-chlorobenzyloxycarbonyl or 2-bromobenzyloxycarbonyl,
- V is 2-chlorocarboxybenzyloxy, benzyloxycarbonyl, 2-bromocarboxybenzyloxy or 2,4-dichlorocarbobenzyloxy, and
- X is D-ala or α-ala.

19. A resin peptide having the structure

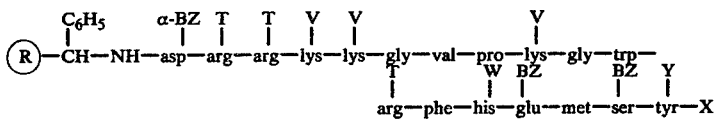

where
- Ⓡ is dinvylbenzene crosslinked polystyrene,
- BZ is benzyl, p-methoxybenzyl, p-chlorobenzyl, p-nitrobenzyl or benzylhydryl,
- Y is H,benzyl,benzyloxycarbonyl, 2-chlorobenzyloxycarbonyl or 2-bromobenzyloxycarbonyl, and
- V is 2-chlorocarboxybenzyloxy, benzyloxycarbonyl, 2-bromocarboxybenzyloxy or 2,4-dichlorocarbobenzyloxy, and
- X is D-ala or β-ala.

* * * * *